(12) United States Patent
Olson et al.

(10) Patent No.: US 11,331,137 B2
(45) Date of Patent: *May 17, 2022

(54) CATHETER WITH ATRAUMATIC TIP

(71) Applicant: St. Jude Medical, Atrial Fibrillation Division, Inc., St. Paul, MN (US)

(72) Inventors: Eric S. Olson, Maplewood, MN (US); James V. Kauphusman, Champlin, MN (US); Linda K. Nemec, Andover, MN (US); Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/941,811

(22) Filed: Mar. 30, 2018

(65) Prior Publication Data
US 2018/0280081 A1    Oct. 4, 2018

Related U.S. Application Data

(60) Continuation of application No. 15/336,012, filed on Oct. 27, 2016, now Pat. No. 9,949,793, which is a
(Continued)

(51) Int. Cl.
*A61B 18/14*     (2006.01)
*A61M 25/00*    (2006.01)
(Continued)

(52) U.S. Cl.
CPC ..... *A61B 18/1492* (2013.01); *A61M 25/0041* (2013.01); *A61M 25/0054* (2013.01);
(Continued)

(58) Field of Classification Search
CPC .......... A61B 18/1492; A61M 25/0041; A61M 25/0054; A61M 25/0074; A61M 25/01; A61M 25/09
(Continued)

(56) References Cited

U.S. PATENT DOCUMENTS 4,385,635 A    5/1983    Ruiz
4,863,442 A    9/1989    DeMello et al.
(Continued)

FOREIGN PATENT DOCUMENTS

EP    0631791 A1    1/1995
EP    2332476 A1    6/2011
(Continued)

OTHER PUBLICATIONS

English Language of Abstract of JP 2011120912 A.
(Continued)

*Primary Examiner* — Daniel L Cerioni
(74) *Attorney, Agent, or Firm* — Dykema Gossett PLLC (57) ABSTRACT

A medical device is provided comprising a shaft comprising a first segment and a second segment. The first segment is configured to buckle upon application of a first critical force. The second segment includes an outer surface and an inner surface and is configured to buckle upon application of a second critical force. The second critical force is lower than the first critical force. The medical device further comprises a coil disposed radially inwardly of the inner surface of the second segment.

16 Claims, 5 Drawing Sheets

Related U.S. Application Data division of application No. 14/580,435, filed on Dec. 23, 2014, now Pat. No. 9,649,155, which is a continuation of application No. 13/341,388, filed on Dec. 30, 2011, now Pat. No. 8,945,025.

(51) Int. Cl.
*A61M 25/01* (2006.01)
*A61M 25/09* (2006.01)
*A61B 18/00* (2006.01)
*A61B 90/00* (2016.01)

(52) U.S. Cl.
CPC ........ *A61M 25/0074* (2013.01); *A61M 25/01* (2013.01); *A61M 25/09* (2013.01); *A61B 2018/00351* (2013.01); *A61B 2018/00577* (2013.01); *A61B 2090/065* (2016.02); *A61B 2090/08021* (2016.02); *A61B 2217/007* (2013.01)

(58) Field of Classification Search
USPC .......................................................... 600/585
See application file for complete search history.

(56) References Cited

U.S. PATENT DOCUMENTS

| | | | |
|---|---|---|---|
| 4,886,506 A | 12/1989 | Lovgren et al. | |
| 4,960,411 A | 10/1990 | Buchbinder | |
| 4,963,306 A | 10/1990 | Weldon | |
| 4,985,022 A | 1/1991 | Fearnot et al. | |
| 5,088,991 A | 2/1992 | Weldon | |
| 5,178,158 A | 1/1993 | de Toledo | |
| 5,221,270 A | 6/1993 | Parker | |
| 5,240,537 A | 8/1993 | Bodicky | |
| 5,318,032 A | 6/1994 | Lonsbury et al. | |
| 5,584,821 A | 12/1996 | Hobbs et al. | |
| 5,769,830 A | 6/1998 | Parker | |
| 5,851,464 A | 12/1998 | Davila et al. | |
| 5,865,800 A | 2/1999 | Mirarchi et al. | |
| 5,891,027 A | 4/1999 | Tu et al. | |
| 5,891,114 A | 4/1999 | Chien et al. | |
| 6,165,163 A | 12/2000 | Chien et al. | |
| 6,233,476 B1 | 5/2001 | Strommer et al. | |
| 6,245,053 B1 | 6/2001 | Benjamin | |
| 6,325,790 B1 | 12/2001 | Trotta | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 6,852,261 B2 | 2/2005 | Benjamin | |
| 6,999,809 B2 | 2/2006 | Currier et al. | |
| 7,029,467 B2 | 4/2006 | Currier et al. | |
| 7,197,354 B2 | 3/2007 | Sobe | |
| 7,250,049 B2 | 7/2007 | Roop et al. | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 7,549,975 B2 | 6/2009 | Lee et al. | |
| 7,824,345 B2 | 11/2010 | Euteneuer et al. | |
| 2004/0167442 A1 | 8/2004 | Shireman et al. | |
| 2005/0004523 A1 | 1/2005 | Osborne et al. | |
| 2007/0100332 A1 | 5/2007 | Paul et al. | |
| 2007/0123764 A1 | 5/2007 | Thao et al. | |
| 2007/0123805 A1 | 5/2007 | Shireman et al. | |
| 2007/0179492 A1 | 8/2007 | Pappone | |
| 2007/0270679 A1 | 11/2007 | Nguyen et al. | |
| 2008/0015568 A1 | 1/2008 | Paul et al. | |
| 2008/0027542 A1 | 1/2008 | McQuillan et al. | |
| 2008/0161796 A1 | 7/2008 | Cao et al. | |
| 2008/0249522 A1 | 10/2008 | Pappone et al. | |
| 2008/0275428 A1 | 11/2008 | Tegg et al. | |
| 2009/0030400 A1 | 1/2009 | Bose et al. | |
| 2009/0163904 A1 | 6/2009 | Miller et al. | |
| 2009/0247942 A1 | 10/2009 | Kirschenman | |
| 2009/0247944 A1 | 10/2009 | Kirschenman et al. | |
| 2009/0247993 A1 | 10/2009 | Kirschenman et al. | |
| 2009/0248042 A1 | 10/2009 | Kirschenman | |
| 2010/0022948 A1 | 1/2010 | Wilson et al. | |
| 2010/0168549 A1 | 7/2010 | Pappone | |
| 2010/0168620 A1 | 7/2010 | Klimovitch et al. | |
| 2010/0174177 A1 | 7/2010 | Wu | |
| 2010/0198208 A1 | 8/2010 | Napp et al. | |
| 2010/0256558 A1 | 10/2010 | Olson et al. | |
| 2011/0015569 A1 | 1/2011 | Kirschenman et al. | |
| 2011/0022045 A1 | 1/2011 | Cao et al. | |
| 2011/0156700 A1* | 6/2011 | Kariv .................. G01R 33/007 324/244 |
| 2011/0288392 A1 | 11/2011 | de la Rama et al. | |
| 2012/0028512 A1 | 2/2012 | Weitzig | |
| 2012/0253167 A1 | 10/2012 | Bonyak | |
| 2012/0265054 A1 | 10/2012 | Olson | |
| 2013/0066193 A1 | 3/2013 | Olson et al. | |

FOREIGN PATENT DOCUMENTS

| | | |
|---|---|---|
| JP | H03 228773 A | 10/1991 |
| JP | 2001190681 | 7/2001 |
| JP | 2006223728 | 8/2006 |
| JP | 2006519072 | 8/2006 |
| JP | 2007135645 | 6/2007 |
| JP | 2011062354 | 3/2011 |
| JP | 2011083594 | 4/2011 |
| JP | 2011120912 A | 6/2011 |
| JP | 2011136170 A | 7/2011 |
| WO | WO 2009120982 | 10/2009 |
| WO | WO 2010078453 | 7/2010 |
| WO | WO 2011139589 A2 | 11/2011 |
| WO | WO 2013101258 | 7/2013 |

OTHER PUBLICATIONS

English Language of Abstract of JP 2007135645 (Jun. 7, 2007).
English Language of Abstract of JP 2011083594 (Apr. 28, 2011).
Extended European Search Report, dated Jun. 29, 2015, PCT/US2012/022745.
K. Yokoyama et al., "Novel Contact Force Sensor Incorporated in Irrigated Radiofrequency Ablation Catheter Predicts Lesion Size and Incidence of Steam Pop and Thrombus," Cir Arrhythmia Electrophysiology (Oct. 2008; 1:354-362).
Shah DC et al., "Catheter Tip Force Required to Mechanically Perforate the Cardiac Free Wall," Conference Proceedings of the Heart Rhythm Society (May 2008).
A. Ikeda et al., "Electrogram Parameters (Injury Current, Amplitude and dV/dt) and Impedance are Poor Predictors of Electrode-Tissue Contact Force for Radiofrequency Ablation," Conference Proceedings of the Heart Rhythm Society (May 2008).
R. Cappato et al., "Worldwide Survey of the Methods, Efficacy and Safety of Catheter Ablation Systems for Human Atrial Fibrillation," Circulation (Feb. 2005; 1:1100-1105).
A. Ikeda et al., "Role of Contact Force in Esophageal Injury During Left Atrial Radiofrequency Ablation," Conference Proceedings of the Heart Rhythm Society (May 2008).
A. Ikeda et al., "Radiofrequency Ablation Catheter with Contact Force Sensor Predicts Lesion Size and Incidence of Steam Pop in the Beating Canine Heart," Conference Proceedings of the Heart Rhythm Society (May 2008).
A. Thiagalingam et al., "Importance of Catheter Contact Force During Irrigated Radiofrequency Ablation: Evaluation in a Porcine Ex Vivo Model Using a Force-Sensing Catheter," Journal of Cardiovascular Electrophysiology (Feb. 2010).
Zoarski, Gregg H. et al., "Performance Characteristics of Microcatheter Systems in a Standardized Tortuous Pathway," American Journal of Neuroradiology, Sep. 1998, vol. 19, p. 1571-1576.
International Search Report and Written Opinion, dated May 25, 2012 (PCT/US2012/022745).
International Preliminary Report on Patentability, dated Jul. 1, 2014 (PCT/US2012/022745).
English Language of Abstract of JP 2001190681 (Jul. 17, 2001).
English Language of Abstract of JP 2006223728 (Aug. 31, 2006).

(56) References Cited

OTHER PUBLICATIONS

English Language of Abstract of JP 2006519072 (Aug. 24, 2006).
English Language of Abstract of JP 2011062354 (Mar. 31, 2011).
Extended European Search Report, issued in corresponding EP patent application No. EP18183846.7. dated Sep. 4, 2018.

* cited by examiner

CATHETER WITH ATRAUMATIC TIP

CROSS-REFERENCE TO RELATED APPLICATIONS

This application is a continuation of U.S. application Ser. No. 15/336,012, filed 27 Oct. 2016 (the '012 application), now U.S. Pat. No. 9,949,793, which is a divisional of Ser. No. 14/580,435, filed 23 Dec. 2014 (the '435 application), now U.S. Pat. No. 9,649,155, which is a continuation of U.S. application Ser. No. 13/341,388, filed 30 Dec. 2011 (the '388 application), now U.S. Pat. No. 8,945,025. The '012 application, the '435 application and the '388 application are hereby incorporated by reference as though fully set forth herein.

BACKGROUND OF THE INVENTION a. Field of the Invention

The instant disclosure relates generally to medical devices. In particular, the instant disclosure relates to elongate medical devices configured to buckle upon application of a critical force.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias. According to at least one medical study (See, e.g., Ikeda et al., *Radiofrequency Ablation Catheter with Contact Force Sensor Predicts Lesion Size and Incidence of Steam Pop in the Beating Canine Heart*, Conference Proceedings of the Hearth Rhythm Society, May 2008 and Thiagalingam et al., *Importance of Catheter Contact Force During Irrigated Radiofrequency Ablation: Evaluation in a Porcine Ex Vivo Model Using a Force-Sensing Catheter*, Journal of Cardiovascular Electrophysiology, February 2010), the therapeutic force required to create a transmural lesion can be about 20 to about 50 grams-force.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features, and in other examples a robotic system may be used to manipulate and/or operate the catheter. Recent advances in the robotic control of catheters and the like allow advancement, retraction, and various deflections and/or steering to be controlled robotically.

In order to facilitate the advancement of catheters through a patient's vasculature, the simultaneous application of torque at the proximal end of the catheter and the ability to selectively deflect the distal tip of the catheter in a desired direction can permit medical personnel (either through manual operation or through robotic control) to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pull wire attached at the distal end of the catheter that extends to a control handle or robotic system that controls the application of tension on the pull wire.

In catheter designs, it can be important to have sufficient flexibility in the catheter shaft to allow the catheter to follow the inherent curvature of the vasculature or endocardium without puncturing vascular tissue and/or cardiac tissue. The perforation of vascular tissue and/or cardiac tissue during cardiac mapping can be a problem in the practice of cardiac electrophysiology. A perforation in the cardiac tissue can result in pericardial effusion or the abnormal accumulation of fluid in the pericardial space and possible cardiac tamponade, which can be life threatening to the patient. The myocardium of the left atrium of the heart is particularly thin and is susceptible to perforation. According to at least one medical study (See, e.g., Shah et al., *Catheter Tip Force Required to Mechanically Perforate the Cardiac Free Wall*, Conference Proceedings of the Hearth Rhythm Society, May 2008), perforation of cardiac tissue can begin to occur with about 100 grams-force. However, other medical studies indicate that perforation of cardiac tissue may begin to occur with even less than about 100 grams-force.

Current catheter designs have concentrated on the use of force or contact sensing to carefully monitor and thereby limit the amount of force delivered during ablation in order to create safe and efficacious lesions. However, such force or contact sensing designs may not consistently provide completely accurate force measurements and can potentially register false positive detections of excessive force and false negatives in which excessive force is not preemptively avoided. Moreover, force or contact sensing systems may report a high force detection too late to prevent perforation. When a high force is generated, even if this force is reported instantaneously by the force or contact sensing systems, the damage may have been caused immediately giving the operator no opportunity to reduce the force.

There is therefore a need to minimize and/or eliminate one or more of the problems as set forth above. A preferable solution would be to avoid the problem of high catheter force altogether.

BRIEF SUMMARY OF THE INVENTION

It is desirable to design a catheter having a mechanical solution for lowering the risk or reducing the likelihood of the catheter from perforating cardiac tissue, rather than being solely dependent on force or contact sensing to identify when a threshold amount of force is being applied to the catheter that is likely to result in perforation of cardiac tissue. In particular, it would be desirable to design a catheter having at least a portion thereof with a relatively low maximum or critical force that causes buckling. It would be desirable for at least a portion of the catheter to be configured to transmit sufficient therapeutic force to create a transmural lesion, while still being configured to buckle upon application of a force that would be sufficient to perforate cardiac tissue or upon application of a force lower than that which would be sufficient to perforate cardiac tissue. Accordingly, it would be desirable for the maximum or critical force that causes buckling of the catheter to be between the maximum amount of force required to create a transmural lesion (e.g., about 50 grams-force according to some medical studies, although other amounts may be possible) and the minimum amount of force that can cause perforation of the cardiac wall (e.g., about 100 grams-force according to some medical studies or even about 50 grams-force according to other medical studies). For example and without limitation, it would be desirable for at least a portion of the catheter to be configured to buckle upon application of a maximum or critical force that is about 50 grams-force to about 100 grams-force. A catheter configured to buckle under a maximum or critical force that causes buckling between about 50 grams-force to about 100 grams-force can develop enough force to create a transmural lesion without buckling, but can predictably buckle prior to developing enough force to perforate cardiac tissue. Although a range for the maximum or critical force that causes buckling of a catheter in accordance with an exemplary embodiment of the disclosure is disclosed as being between about 50 grams-force to about 100 grams-force, the range for the maximum or critical force that causes buckling may be lower or higher in accordance with other embodiments of the disclosure. For example and without limitation, the range for the maximum or critical force that causes buckling of a catheter in accordance with other exemplary embodiments of the disclosure can be about 50 to about 60 grams-force in some embodiments. For example and without limitation, the range for the maximum or critical force that causes buckling of a catheter in accordance with other exemplary embodiments of the disclosure can be about 20 grams-force to about 50 grams-force in some embodiments. For example and without limitation, the maximum or critical force that causes buckling of a catheter in accordance with other exemplary embodiments of the disclosure can be about 40 grams-force in some embodiments.

A medical device is provided comprising a shaft comprising a first segment and a second segment. The first segment can have an outer surface and an inner surface. The first segment can be configured to buckle upon application of a first critical force thereto. The second segment can include an outer surface and an inner surface. The second segment is configured to buckle upon application of a second critical force thereto, wherein the second critical force is lower than the first critical force. For example and without limitation, the second critical force is in the range of about 40 grams-force to about 100 grams-force. The second segment can be configured to transmit force in the range of at least about 20 grams-force to about 50 grams-force to tissue contacting the second segment. For example and without limitation the second segment comprises polyether block amides. For example and without limitation, the second segment has a hardness between about 25 and about 35 on a Shore D scale. Although a first and second segment are mentioned in detail, the medical device can include additional segments in accordance with various embodiments of the disclosure. For example and without limitation, the medical device can include a third segment configured to buckle upon application of a third critical force thereto. The third critical force can be different than both the first critical force and the second critical force. The third segment can also include an outer surface and an inner surface.

In accordance with some embodiments of the disclosure, the second segment has a distal end formed in the shape of a pigtail. In accordance with other embodiments of the disclosure, the second segment has at least one electrode disposed on the second segment. For example and without limitation, the a first electrode can be disposed on the distal end of the second segment. Additional electrodes may be disposed on the second segment proximally of the first electrode. In an embodiment of the disclosure, the second segment may include about four electrodes.

The medical device further comprises a coil disposed radially inwardly of the inner surface of the second segment. The coil can be separate from the first segment and from the second segment in accordance with some embodiments of the disclosure. The coil can be configured to prevent collapsing of an irrigation lumen within the coil. The coil can also be configured to maintain the amount of force transmitted by the second segment to tissue contacting the second segment even after an application of the second critical force to the second segment. The coil can have a proximal end and a distal end. In some embodiments of the disclosure, spacing between adjacent turns of the coil is greater at the distal end of the coil than the proximal end of the coil. In some embodiments of the disclosure, a first diameter of the coil at the proximal end is greater than a second diameter of the coil at the distal end. In some embodiments of the disclosure, at least a portion of the proximal end of the coil is welded to the second segment and at least a portion of the distal end of the coil is welded to the second segment.

In some embodiments of the disclosure, the second segment of the medical device may further comprise a curve at a select location along a length of the medical device. For example and without limitation, the curve can be in the range of about 5 degrees to about 25 degrees in some embodiments of the disclosure. For example and without limitation, the curve can be defined by the angle between a first portion of the medical device on a first side of the curve and a second portion of the medical device on a second opposing side of the curve. In some embodiments of the disclosure, the medical device can further comprise a fluid lumen disposed radially inwardly of the coil. In some embodiments of the disclosure, the medical device can further comprise a force/contact sensor configured to detect an amount of force provided by the medical device. In some embodiments of the disclosure, the second segment can comprise a first critical section on which a first plurality of electrodes are disposed and a second critical section on which a second plurality of electrodes are disposed. The medical device can further comprise a sensor configured to generate a signal indicative of a bend angle between the first critical section and the second critical section of the second segment.

A medical device is provided comprising a shaft comprising a first segment and a second segment. The first segment is configured to buckle upon application of a first critical force thereto. The second segment is configured to buckle upon application of a second critical force thereto. The second critical force is lower than the first critical force and is in the range of about 40 grams-force to about 100 grams-force. The medical device can further comprise at least one electrode disposed on at least one of the first and second segments of the shaft. The medical device can further comprise a coil disposed radially inwardly of an inner surface of the second segment, wherein the coil is separate from both the first segment and the second segment, and wherein the second segment is configured to transmit force in the range of at least about 20 grams-force to about 50 grams-force to tissue contacting the second segment after application of the second critical force to the second segment. The medical device can further comprise a fluid lumen disposed radially inwardly of the coil.

A medical device is provided comprising a shaft comprising a first segment and a second segment. The first segment is configured to buckle upon application of a first critical force thereto. The second segment is configured to buckle upon application of a second critical force thereto. The second critical force is lower than the first critical force. The medical device can further comprise a means for maintaining the amount of force transmitted by the second segment to tissue contacting the second segment after an application of the second critical force to the second segment. The medical device can further comprise a means for preferentially buckling the second segment in a select manner, such as a deflection preference element comprising a curve at a select location along the length of the medical device.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the teen "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The instant disclosure generally relates to irrigated ablation electrode assemblies. For purposes of this description, similar aspects among the various embodiments described herein will be referred to by similar reference numbers. As will be appreciated, however, the structure of the various aspects can be different among the various embodiments.

Figure 1:
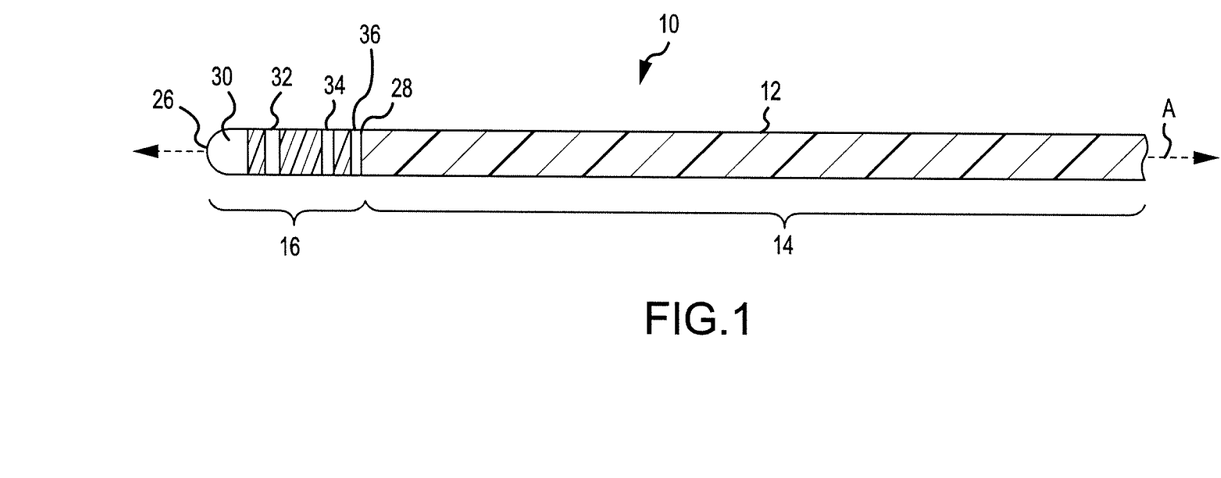
FIG. 1 is a schematic view of a medical device in accordance with a first embodiment of the disclosure.

Referring now to FIG. 1, a schematic view of a medical device 10 in accordance with an embodiment of the disclosure is illustrated with differences in cross-hatching showing potential differences in materials and/or structure. The medical device 10 may be a catheter comprising an elongated shaft 12 having a first segment 14 and a second segment 16. Although a medical device 10 comprising two segments 14, 16 are mentioned in detail, additional segments can be utilized in connection with medical device 10 in accordance with various other embodiments of the invention. Also, although the embodiment shown in FIG. 1 depicts medical device 10 as a catheter, it can be appreciated that the medical device 10 can comprise any medical device designed to pass through an opening or body lumen. For example and without limitation, the medical device 10 can comprise catheters (e.g., therapeutic, diagnostic, and/or guide catheters), sheaths, introducers (e.g., steerable and/or precurved introducers), epicardial devices, endoscopic devices, laproscopic devices, as well as any other medical devices. While the devices and/or methods described herein may be especially useful in connection with robotically controlled systems, such devices and/or methods can also be incorporated in connection with manually manipulated medical devices in order to provide an added level of safety for the physician and patient, for example.

The length of medical device 10, shaft 12, first segment 14, and/or second segment 16 or portions thereof are typically dictated by the length and flexibility characteristics desired in the final medical device 10. The cross-sectional shape of medical device 10, shaft 12, first segment 14, and/or second segment 16 or portions thereof are typically dictated by the desired characteristics (e.g., flexibility, torque transmission characteristics, etc.) in the final medical device 10 and can vary in accordance with various embodiments of the disclosure. For example, they can have a substantially round cross-sectional shape in some embodiments. However, other cross-sectional shapes or combinations of shapes can be utilized in accordance with other embodiments of the disclosure. For example, the cross-sectional shapes can be oval, rectangular, square, polygonal, or any other suitable shape, or combinations thereof. The diameter of medical device 10, shaft 12, first segment 14, and/or second segment 16 or portions thereof are also typically dictated by the desired characteristics (e.g., flexibility, torque transmission characteristics, etc.) in the final medical device 10 and can vary in accordance with various embodiments of the disclosure. For example, they can have a substantially constant diameter in some embodiments or can have a variable diameter in other embodiments (e.g., linear tapered regions, curvilinear tapered regions, step-wise tapered regions, etc.). For example and without limitation, the medical device 10 can comprise an intracardiac catheters having a diameter of about 8 French or less.

In accordance with an embodiment of the disclosure, the first segment 14 can be a proximal segment of the shaft 12, and the second segment 16 can be a distal segment of the shaft 12. Although this particular configuration is mentioned in detail, in accordance with other embodiments of the disclosure, the first segment 14 can be a distal segment of the shaft 12, and the second segment 16 can be a proximal segment of the shaft 12.

Figure 2:
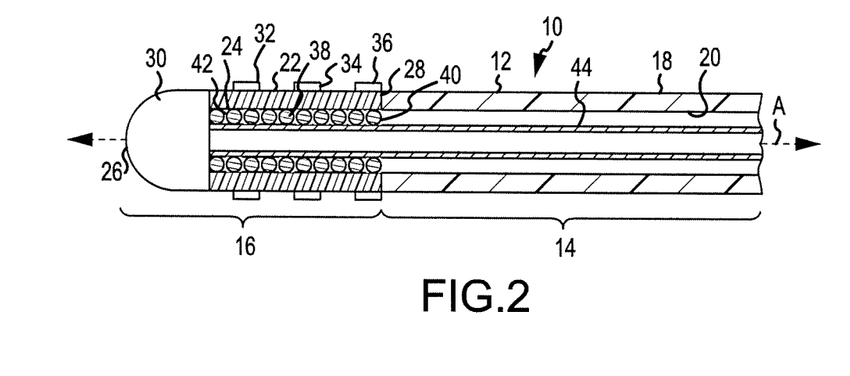
FIG. 2 is a cross-sectional view of the medical device of FIG. 1.

Referring now to FIG. 2, the first segment 14 includes an outer surface 18 and an inner surface 20. The first segment 14 can comprise a polymer in accordance with an embodiment of the disclosure. The polymer can comprise, for example and without limitation, polyether block amides such as those sold under the trademark PEBAX® and generally available from Arkema France. Although polyether block amides are mentioned in detail, the polymer can comprise any number of other polymers such as polytetrafluoroethylene (PTFE), fluorinated ethylene propylene (FEP), polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, silicones, polyethylene, Marlex high-density polyethylene, linear low density polyethylene (for example REXELL®), polyetheretherketone (PEEK), polyimide (PI), polyetherimide (PEI), other suitable materials, or mixtures, combinations, or copolymers thereof. In some embodiments the first segment 14 can include a liquid crystal polymer (LCP) blended with other polymers to enhance torqueability. Although polymers are mentioned in detail, the first segment 14 can comprise any other number of materials in other embodiments. For example and without limitation, the first segment 14 can comprise metals, metal alloys, polymers, or combinations or mixtures thereof. Some examples of suitable metals and metal alloys include stainless steel, such as 304v stainless steel; nickel-titanium alloy, such as "Nitinol," nickel-chromium alloy, nickel-chromium-iron 65 alloy, cobalt alloy, or the like; or other suitable material. The entire first segment 14 can be made of the same material, or the composition of the first segment 14 can vary along a length of the first segment 14. At least a portion of the material comprising the first segment 14 can be contoured (e.g., laser cut) to provide unique shapes that can have rotational rigidity, but have low column strength or other desirable characteristics in accordance with some embodiments of the disclosure. For example and without limitation, at least a portion of the material comprising the first segment 14 can comprise a helically shaped body having alternately spaced projections extending away from the helically shaped body in opposite directions from one another along the length of the helix. For example, a first set of projections can extend distally, and a second set of projections can extend proximally, with the first set of projections offset from and positioned between the second set of projections. Recesses extending between projections can be inversely shaped with respect to an outer contour of the projections. The projections and recesses can be trapezoidal in shape in accordance with some embodiments of the disclosure, but other shapes for the projections and recesses could be used in alternative embodiments. The projections may extend into recesses from an adjacent section of the helical body to form an interlocking arrangement.

In general, the first segment 14 can comprise materials chosen to ensure that the first segment 14 is relatively stiff for pushability and torqueability. For example and without limitation, the first segment 14 can have a hardness between about 60 and about 90 on a Shore D scale. For example and without limitation, the first segment 14 can have a Shore D durometer of about 75. Although these particular amounts are disclosed for the hardness of the first segment 14, the hardness of the first segment 14 can be greater or less in accordance with various embodiments of the disclosure. The entire first segment 14 can have the same Shore D durometer in an embodiment of the disclosure, or the hardness of the first segment 14 can vary along the length of the first segment 14 in accordance with other embodiments of the disclosure. The first segment 14 has a first critical force sufficient to cause buckling of the first segment 14. For example and without limitation, the first critical force sufficient to cause buckling of the first segment 14 can be greater than 100 grams-force. In particular, the first critical force sufficient to cause buckling of the first segment 14 can be between about 200 grams-force and about 660 grams-force. Although these particular amounts are disclosed for the first critical force, the first critical force of the first segment 14 can be greater or less in accordance with various embodiments of the disclosure. The entire first segment 14 can be configured to have the same first critical force, or the first critical force of the first segment 14 can vary along the length of the first segment 14. The first critical force can be fine-tuned to any desired range by altering the durometer of the materials used for the first segment 14 and/or modifying the configuration of the first segment 14 through the use of laser-cutting, for example.

Now referring to FIGS. 1-2, the second segment 16 includes an outer surface 22 and an inner surface 24. The second segment 16 further includes a distal end 26 and a proximal end 28. The second segment 16 can comprise a polymer in accordance with an embodiment of the disclosure. The polymer can comprise, for example and without limitation, polyether block amides such as those sold under the trademark PEBAX® and generally available from Arkema France. Although polyether block amides are mentioned in detail, the polymer can comprise any number of other polymers such as PTFE, FEP, polyurethane, PP, PVC, polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, silicones, polyethylene, Marlex high-density polyethylene, linear low density polyethylene (for example REXELL®), PEEK, PI, PEI, other suitable materials, or mixtures, combinations, or copolymers thereof. In some embodiments the second segment 16 can include an LCP blended with other polymers to enhance torqueability. Although polymers are mentioned in detail, the second segment 16 can comprise any other number of materials in other embodiments. For example and without limitation, the second segment 16 can comprise metals, metal alloys, polymers, or combinations or mixtures thereof. Some examples of suitable metals and metal alloys include stainless steel, such as 304v stainless steel; nickel-titanium alloy, such as "Nitinol," nickel-chromium alloy, nickel-chromium-iron 65 alloy, cobalt alloy, or the like; or other suitable material. The entire second segment 16 can be made of the same material, or the composition of the second segment 16 can vary along a length of the second segment 16. At least a portion of the material comprising the second segment 16 can be contoured (e.g., laser cut) to provide unique shapes that can have rotational rigidity, but have low column strength or other desirable characteristics in accordance with some embodiments of the disclosure. For example and without limitation, at least a portion of the material comprising the second segment 16 can comprise a helically shaped body having alternately spaced projections extending away from the helically shaped body in opposite directions from one another along the length of the helix. For example, a first set of projections can extend distally, and a second set of projections can extend proximally, with the first set of projections offset from and positioned between the second set of projections. Recesses extending between projections can be inversely shaped with respect to an outer contour of the projections. The projections and recesses can be trapezoidal in shape in accordance with some embodiments of the disclosure, but other shapes for the projections and recesses could be used in alternative embodiments. The projections may extend into recesses from an adjacent section of the helical body to form an interlocking arrangement.

The second segment 16 generally provides the medical device 10 with a region having decreased column strength or increased flexibility as compared to the first segment 14. For example and without limitation, the second segment 16 can have a hardness between about 25 and about 35 on a Shore D scale. In a preferred embodiment, the second segment 16 can have a Shore D durometer of about 25. Although these particular amounts are disclosed for the hardness of the second segment 16, the hardness of the second segment 16 can be greater or less in accordance with various embodiments of the disclosure. The entire second segment 16 can have the same Shore D durometer in some embodiments of the disclosure, or the hardness of the second segment 16 can vary along the length of the second segment 16 in other embodiments of the disclosure. Because of its decreased Shore D durometer hardness, the second segment 16 is more flexible than first segment 14. This feature allows medical device 10 to buckle at second segment 16.

The second segment 16 may be configured so that it can buckle upon application of a second critical force to the second segment 16. The second critical force can be applied to the second segment 16 of the medical device 10 at any approach angle of the medical device 10. For example and without limitation, the application of the second critical force at a glancing angle can have a component of force along the axis of the medical device 10 and a component of force tangent to the direction of the second segment 16 of the medical device 10. Mechanically, it is the tangential component of the force that causes the buckling of the second segment 16. For another example and without limitation, the application of the second critical force on the axis of the medical device 10 (e.g., straight on) can have at least a momentary tangential force that can cause the cascade of failure (e.g., buckling) to occur. Buckling is generally understood to be a change in shape of the medical device 10 or any other type of altering of position or of configuration of medical device 10 that results in at least some lateral displacement of at least a portion of second segment 16. Although lateral deflection is mentioned in detail, other forms of buckling can include spiraling, looping, or helical buckling. Buckling of the second segment 16 can divert force away from or prevent force from being directly or indirectly transmitted from second segment 16 to cardiac tissue. Diverting or preventing the transmission of force to cardiac tissue can result in a reduced or nominal amount of displacement of the cardiac tissue. As force is applied to the first segment 14 of the medical device 10 in the distal direction, the medical device 10 advances distally. When additional distal force is diverted from the cardiac tissue by the buckling of second segment 16, the second segment 16 acts to limit the amount of force that can be transmitted from the first segment 14 to the cardiac tissue, thereby helping to avoid undesirable perforation of the cardiac tissue. Buckling of the second segment 16 can also increase the surface area of the medical device 10 in contact with the tissue, thereby distributing the applied force over a greater area and reducing pressure, which provides an additional safety factor. Buckling of the second segment 16 can also increase contact area during ablation, which can create large lesions. In addition, the second segment 16 can be configured to absorb any energy caused by the medical device 10 making contact with tissue under cardiac motion which might otherwise cause the medical device 10 to lose contact with the tissue, thereby allowing the medical device 10 to be kept in contact with the tissue even under cardiac motion and providing a uniform force. Accordingly, the second segment 16 can prevent the medical device 10 from breaking contact during ablation/mapping for better lesions and recordation of cardiac signals.

Figure 7:
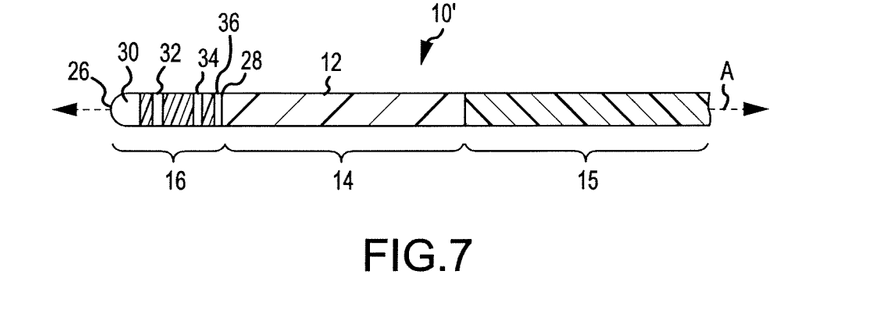
FIG. 7 is a schematic view of a medical device in accordance with a fifth embodiment of the disclosure.
Figure 8:
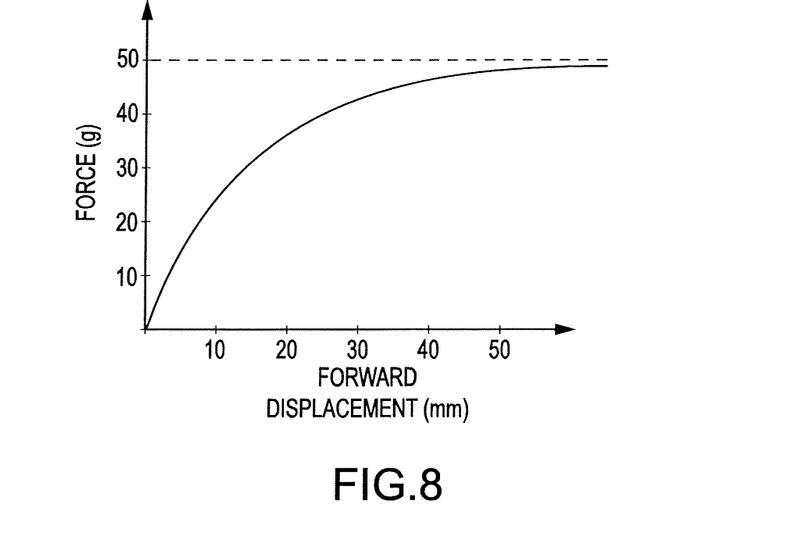
FIG. 8 is an exemplary graph showing force as a function of the forward displacement of the medical device of FIG. 1.

As noted above, the second segment 16 may be configured so that it can buckle upon application of a second critical force to the second segment 16. The second critical force of the second segment 16 is lower than the first critical force of the first segment 14. The second critical force that causes buckling of the second segment 16 of the medical device 10 is configured to be between the amount of force required to create a transmural lesion (i.e., about 20 to about 50 grams-force according to some medical studies, but can be more or less) and the minimum amount of force that can cause perforation of cardiac tissue (i.e., about 100 grams-force according to some medical studies and even about 50 grams-force according to other medical studies). For example and without limitation, the second critical force sufficient to cause buckling of the second segment 16 of the medical device 10 can be in the range of about 40 grams-force to about 100 grams-force. Although these particular amounts are disclosed for the second critical force, the second critical force of the second segment 16 can be greater or less in accordance with various embodiments of the disclosure. For example and without limitation, the second critical force sufficient to cause buckling of the second segment 16 of the medical device 10 can be in the range of about 50 grams-force to about 60 grams-force in accordance with some embodiments of the disclosure. For example and without limitation, the second critical force sufficient to cause buckling of the second segment 16 of the medical device 10 can be in the range of about 20 grams-force to about 50 grams-force in accordance with some embodiments of the disclosure. For example and without limitation, the second critical force sufficient to cause buckling of the second segment 16 of the medical device 10 can be about 40 grams-force. The second segment 16 can be configured to develop and transmit sufficient force to targeted cardiac tissue to create a transmural lesion in cardiac tissue without buckling, but would be configured to predictably buckle prior to developing and transmitting force sufficient to perforate cardiac tissue. In this way, the second segment 16 can be engineered to buckle at a predetermined second critical force and/or be tuned to buckle at a specific force. For example, it can be desirable to manufacture or configure the second segment 16 so that it will buckle before the pushing forces become high enough that second segment 16 could displace and perforate, for example, a blood vessel or other cardiac tissue. The entire second segment 16 can be configured to have the same second critical force, or the second critical force of the second segment 16 can vary along the length of the second segment 16. The second critical force can be fine-tuned to any desired range by altering the durometer of the materials used for the second segment 16 and/or modifying the configuration of the second segment 16 through the use of laser-cutting, for example. Although the medical device 10 is described and generally illustrated as including one second segment 16, the medical device 10 can include any number of segments, zones, and/or locations having a critical force sufficient to cause buckling of the segment, zone, and/or location that is lower than the first critical force of the first segment 14. In this way, the medical device 10 can have one or more such segments, zones, and/or locations configured for buckling. For example and without limitation, as generally illustrated in FIG. 7, a medical device 10' can comprise a third segment 15. The third segment 15 can also include an inner surface and an outer surface. The third segment 15 can be configured to buckle upon application of a third critical force. The third critical force can be different than the first critical force in accordance with some embodiments of the disclosure. The third critical force can be different than the second critical force in accordance with some embodiments of the disclosure. FIG. 8 is an exemplary graph showing force as a function of the forward displacement of the medical device 10, 10' after the medical device comes into contact with tissue. For example and without limitation, FIG. 8 generally illustrates a rise in force that asymptotically approaches the second critical force or buckling force.

Still referring to FIGS. 1-2, the medical device 10 can comprise one or more electrodes disposed on the second segment 16. Although one or more electrodes being disposed on the second segment 16 is mentioned in detail, one or more electrodes can be disposed on the first segment 14 in accordance with some embodiments of the disclosure. A first electrode 30 can be disposed on the distal end 26 of the second segment 16 in accordance with an embodiment of the disclosure. The first electrode 30 can comprise an ablation electrode disposed at the extreme distal end 26 of the second segment 16 and can be referred to as a tip electrode. A distal end of the first electrode 30 can be partially spherical or generally hemispherical in shape in accordance with an embodiment of the disclosure. Electrode 30 can comprise an electrically conductive material that can be generally resistant to corrosion and is biocompatible. For example and without limitation, electrode 30 can be constructed from platinum. However, other conductive materials, such as gold, stainless steel, or others known in the art can be similarly used. The first electrode 30 can include a corresponding conductor.

In accordance with some embodiments of the disclosure, the distal end 26 of the second segment 16 can comprise a tip element as described and illustrated in at least FIG. 9 of U.S. Patent Application Publication No. 2010/0174177 entitled "Magnetically Guided Catheter," the entire disclosure of which is incorporated herein. In such an embodiment of the disclosure, the tip element can comprise a helically shaped body having alternately spaced projections extending away from the helically shaped body in opposite directions from one another along the length of the helix. For example, a first set of projections can extend distally, and a second set of projections can extend proximally, with the first set of projections offset from and positioned between the second set of projections. Recesses extending between projections can be inversely shaped with respect to an outer contour of the projections. The projections and recesses can be trapezoidal in shape in accordance with some embodiments of the disclosure, but other shapes for the projections and recesses could be used in alternative embodiments. The projections may extend into recesses from an adjacent section of the helical body to form an interlocking arrangement.

At least a second electrode 32 can be disposed on the second segment 16 of the medical device 10 in accordance with an embodiment of the disclosure. The second electrode 32 can be disposed proximally of the first electrode 30. A plurality of electrodes (e.g., second electrode 32, third electrode 34, and fourth electrode 36) can be disposed on the second segment 16 of the medical device 10 in accordance with an embodiment of the disclosure. The plurality of electrodes 32, 34, 36 can be disposed along a longitudinal axis A of the medical device 10. Second electrode 32 can be disposed proximally of the first electrode 30, third electrode 34 can be disposed proximally of the second electrode 32, and fourth electrode 34 can be disposed proximally of the third electrode 34. Each of the plurality of electrodes 32, 34, 36 can comprise an electrically conductive material that can be generally resistant to corrosion and is biocompatible. For example and without limitation, each electrode 32, 34, 36 can be constructed from platinum. However, other conductive materials, such as stainless steel or others known in the art can be similarly used. Each of the plurality of electrodes 32, 34, 36 can comprise a ring electrode as generally known in the art in accordance with some embodiments of the disclosure. Each of the plurality of electrodes 32, 34, 36 can include a corresponding wire extending toward a proximal end of the medical device 10 for connection to an energy generator in accordance with some embodiments of the disclosure.

Each of electrodes 32, 34, 36 can comprise a positioning electrode used, for example, with a visualization, navigation, and mapping system and can be configured to provide a signal indicative of a position and/or orientation of at least a portion of the medical device 10. The visualization, navigation, and/or mapping system with which the electrodes 32, 34, 36 can be used can comprise an electric field-based system, or sometimes referred to as an impedance-based system, such as, for example, that having the name ENSITE NAVX™ (aka ENSITE™ 'Classic' as well as newer versions of the ENSITE™ system, denoted as ENSITE VELOCITY™) and available from St. Jude Medical, Inc. and as generally shown with reference to U.S. Pat. No. 7,263,397 entitled "Method and Apparatus for Catheter Navigation and Location and Mapping in the Heart," the entire disclosure of which is incorporated herein by reference. In accordance with an electric field-based system, the electrodes 32, 34, 36 can be configured to be responsive to an electric field transmitted within the body of the patient. The electrodes 32, 34, 36 can be used to sense an impedance at a particular location and transmit a representative signal to an external computer or processor. In other exemplary embodiments, however, the visualization, navigation, and/or mapping system can comprise other types of systems, such as, for example and without limitation: a magnetic field- and current-based system such as the CARTO™ 3 System (with current- and magnetically-driven or receptive electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS™ system or MEDIGUIDE™ technology from St. Jude Medical, Inc., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the catheter can be configured to include field sensors (e.g., coils) responsive to a magnetic field transmitted by a medical positioning system (MPS) through the body of the patient to sense the strength of the field at a particular location and transmit a representative electrical signal to an external computer or processor, which is configured to determine a position and/or orientation (P&O) associated with the sensor, which sensor may be attached to a medical device. Such field sensors can comprise one or more conductive coils (not shown) located on or within the catheter shaft 12 in a magnetic field-based system where the field sensor comprising the one or more conductive coils is coupled to the above-mentioned external computer or processor by electric conductors for determining a position and/or orientation. In an embodiment, the P&O may be based on capturing and processing the signals received from the field sensor while in the presence of a controlled low-strength alternating current (AC) magnetic field. The field sensors may each comprise one or more magnetic field detection coil(s), and it should be understood that variations as to the number of coils, their geometries, spatial relationships, the existence or absence of cores and the like are possible. From an electromagnetic perspective, all sensors are created equal: voltage is induced on a coil residing in a changing magnetic field, as contemplated here. As noted above, a combination electric field-based and magnetic field-based system such as the CARTO™ 3 System (available from Biosense Webster), and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the catheter can include both electrodes 32, 34, 36 as one or more impedance-based electrodes and one or more magnetic field-sensing coils. For example and without limitation, electrodes 32, 34, 36 can be used in accordance with the systems and methods described in prior filed commonly owned U.S. patent application Ser. No. 13/087,203, entitled "System and Method for Registration of Multiple Navigation Systems to a Common Coordinate Frame" and filed on Apr. 14, 2011, and U.S. patent application Ser. No. 13/231,284, entitled "Catheter Navigation Using Impedance and Magnetic Field Measurements" and filed on Sep. 13, 2011, each of which is hereby incorporated by reference in its entirety as though fully set forth herein.

Figure 3:
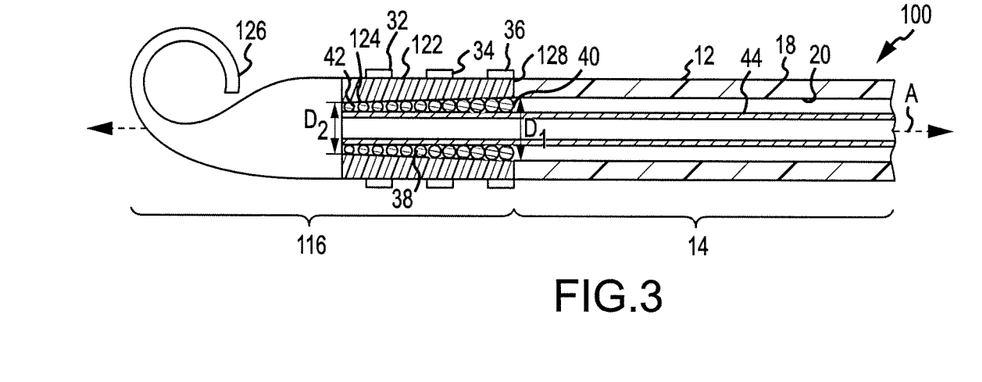
FIG. 3 is a cross-sectional view of a medical device in accordance with a second embodiment of the disclosure.

Referring now to FIG. 3, a cross-sectional view of a medical device 100 in accordance with a second embodiment of the disclosure is generally illustrated. The medical device 100 is substantially identical to the medical device 10 of FIGS. 1-2, except that the distal end 126 of the second segment 116 is formed in the shape of a curled pigtail instead of a tip electrode having a substantially spherical or hemispherical end. The distal end 126 of the second segment 116 can comprise a highly flexible plastic in accordance with an embodiment of the disclosure. For example and without limitation, the distal end 126 of the second segment 116 can comprise a polymer. The polymer can comprise, for example and without limitation, polyether block amides such as those sold under the trademark PEBAX® and generally available from Arkema France. Although polyether block amides are mentioned in detail, the polymer can comprise any number of other polymers such as PTFE, FEP, polyurethane, PP, PVC, polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, silicones, polyethylene, Marlex high-density polyethylene, linear low density polyethylene (for example REXELL®), PEEK, PI, PEI, or other suitable materials, or mixtures, combinations, or copolymers thereof. Additionally, in at least one embodiment, the distal end 126 of the second segment 16, 116 may be an electrode, and, accordingly, may be made from a flexible, conductive material, such as a conductive polymer. Although these particular materials are mentioned in detail, the distal end 126 of the second segment 116 can comprise any number of other materials in accordance with various embodiments of the disclosure. A second segment 116 formed in the shape of a pigtail can be a particularly atraumatic configuration for the distal end of the second segment 116 since it can distribute force over a larger region than a distal end, such as a distal end 26 described above, having a substantially spherical or hemispherical end.

Figure 4:
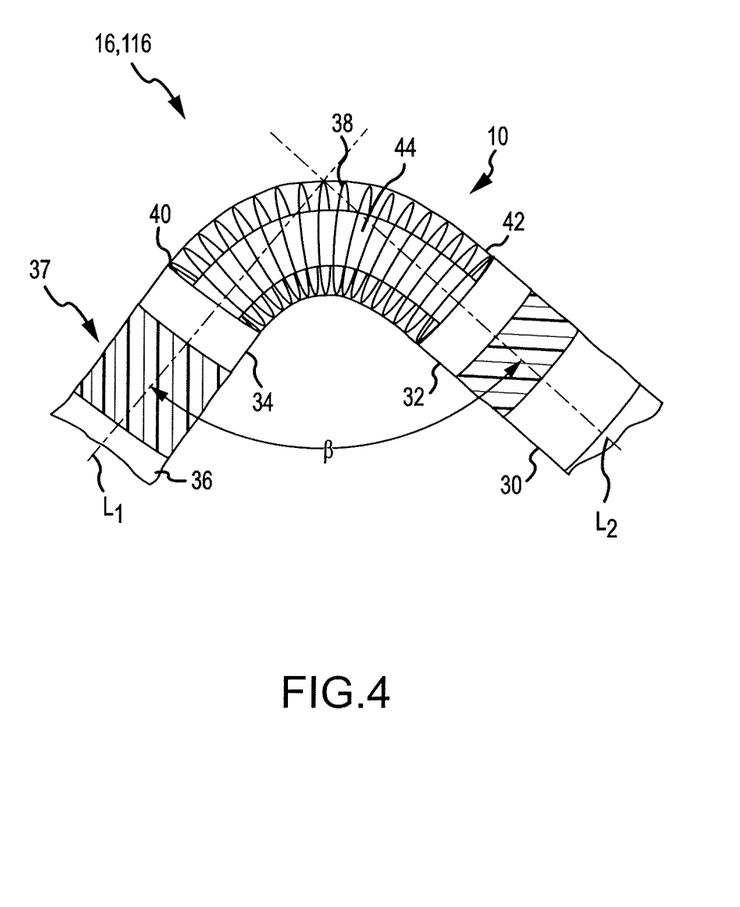
FIG. 4 is a partially transparent perspective view of a distal segment of a medical device according to various embodiments of the disclosure.

Referring now to FIGS. 2-4, medical device 10, 100 may also comprise a coil 38. The coil can be configured to prevent collapsing of an irrigation lumen disposed within the coil as described in more detail hereinbelow. The coil 38 comprises a means for maintaining the amount of force transmitted by the second segment 16, 116 to the first segment 14 and/or tissue contacting at least a portion of the second segment 16, 116 after an application of the second critical force to the second segment 16, 116 that is sufficient to cause buckling of the second segment 16, 116. Without the means for maintaining the amount of force transmitted by the second segment 16, 116 after an application of the second critical force to the second segment 16, 116 that is sufficient to cause buckling of the second segment 16, 116, the medical device 10, 100 would tend to collapse and provide a somewhat constant force afterwards. The coil 38 provides a more uniform force after buckling of the medical device 10, 100 than without. The coil 38 does not significantly increase the second critical force required to cause the second, distal segment 16, 116 to buckle. However, coil 38 is configured to allow second segment 16, 116 to transmit force in the range of at least about 20 grams-force to about 50 grams-force even after application of the second critical force to the second segment 16, 116 sufficient to cause buckling of the second segment 16, 116. In this way, coil 38 is configured to allow medical device 10, 100 to buckle to avoid perforation of cardiac tissue by limiting the amount of force that can be applied by the second segment 16, 116 to the cardiac tissue, while still ensuring that the medical device 10, 100 is able to transmit a minimum amount of force required to create transmural lesions in the tissue. Such an embodiment including coil 38 can result in the predictable and/or recoverable buckling of the medical device 10, 100. The amount of force generated by bending and/or compressing the coil 38 can be used to fine-tune the second critical force that is sufficient to cause buckling of the second segment 16. More significantly in some embodiments of the disclosure, coil 38 can be configured to prevent collapsing of an irrigation lumen within the coil 38 before, after, and/or during a buckling of the second segment 16, 116. Coil 38 may be separate from both the proximal, first segment 14 and from the distal, second segment 16, 116 by use of a reflow procedure, for example. Coil 38 may be disposed within the second segment 16, 116 of medical device 10, 100. For example and without limitation, the coil 38 may be disposed radially inwardly of the inner surface 24, 124 of the second segment 16, 116.

The coil 38 can comprise any number of suitable materials, including, for example and without limitation, metals, metal alloys, polymers, metal-polymer composites, and the like. Some examples of materials include stainless steel, nickel-chromium alloy, nick-chromium-iron alloy, cobalt alloy, platinum, low durometer plastic, and the like. Additional examples of material include straightened super elastic or linear elastic alloy (e.g., nickel-titanium or Nitinol) wire, or alternatively, a polymer material, such as a high performance polymer. The coil 38 can be formed of round wire or flat ribbon ranging in dimensions to achieve the desired characteristics such as flexibility, and can be wound in a generally helical fashion by conventional winding techniques. For example and without limitation, the thickness of the coil 38 can be varied along the length of the coil 38. In some embodiments of the disclosure, the coil 38 can comprise a quad-filer coil which is comprised of multiple coils (e.g., about four coils) that are interleaved together about a common radial axis. A quad-filer coil can be more flexible, have a lower buckling force, and have the ability to operate even in the case of failure (e.g., breakage) of a single coil. In some embodiments of the disclosure, the coil 38 can comprise a tri-filer coil which is comprised of multiple coils (e.g., about three coils) that are interleaved together about a common radial axis. A tri-filer coil can also be more flexible, have a lower buckling force, and have the ability to operate even in the case of failure (e.g., breakage) of a single coil. Although quad-filer and tri-filer coils are mentioned in detail, there may be any number of multiple coils interleaved together for the coil 38 in accordance with various embodiments of the disclosure (e.g., N-filer coil, where N is the number of coils interleaved together). Additionally, a support structure providing similar functionality to that of coil 38 may include a braided set of wires in place of, or in addition to, coil 38.

The coil 38 has a proximal end 40 and a distal end 42. The pitch of adjacent turns of the coil 38 can be tightly wound so that each turn touches the succeeding turn, or the pitch can be set such that the coil 38 is wound in an open fashion. The pitch of adjacent turns of the coil 38 can be substantially constant along the length of the coil 38 from the proximal end 40 to the distal end 42 in accordance with an embodiment of the disclosure and as shown in FIG. 2. In accordance with other embodiments of the disclosure, the pitch between adjacent turns of the coil 38 can vary along the length of the coil 38 from the proximal end 40 to the distal end 42. A variable pitch of the coil 38 can be preferable in some embodiments of the disclosure to help ensure that any buckling of second segment 16, 116 occurs in a smooth and/or continuous fashion or radius, rather than a sharp 90 degree bend or kink that might otherwise occur. A variable pitch of the coil 38 can also be preferable in some embodiments of the disclosure to help ensure that any buckling of second segment 16, 116 occurs at a particular location along the length of the second segment 16, 116. For example and without limitation, the pitch or the spacing between adjacent turns of the coil 38 can be greater near the distal end 42 of the coil 38 than the proximal end 40 of the coil 38, as generally illustrated in FIG. 3, to help ensure that the buckling of second segment 16, 116 occurs closer to the distal end 42 of the coil 38 than to the proximal end 40 of the coil 38 in a smooth, continuous fashion or radius. Accordingly, the coil 38 can have a relatively tight pitch at the proximal end 40 of the coil 38 and a relatively wide pitch at the distal end 42 of the coil 38.

In accordance with some embodiments of the disclosure, the coil 38 can be wound so that the diameter of each turn is substantially constant along the length of the coil 38 from the proximal end 40 to the distal end 42. In accordance with other embodiments of the disclosure, the diameter of each turn can vary along the length of the coil 38 from the proximal end 40 to the distal end 42. A variable diameter of the coil 38 may be preferable in some embodiments to help ensure that any buckling of second segment 16, 116 occurs in a smooth and/or continuous fashion or radius, rather than a sharp 90 degree bend or kink that might otherwise occur. A variable diameter of the coil 38 can also be preferable in some embodiments of the disclosure to help ensure that any buckling of second segment 16, 116 occurs at a particularly location along the length of the second segment 16, 116. For example and without limitation, a first diameter $D_1$ of the turns of the coil 38 at the proximal end 40 can be greater than a second diameter $D_2$ of the turns of the coil 38 at the distal end 42, as generally illustrated in FIG. 3, to help ensure that the buckling of second segment 16, 116 occurs closer to the distal end 42 of the coil 38 than to the proximal end 40 of the coil 38 in a smooth, continuous fashion or radius. Accordingly, the coil 38 can have a relatively larger diameter $D_1$ at the proximal end 40 of the coil 38 and a relatively smaller diameter $D_2$ at the distal end 42 of the coil 38.

At least a portion of the proximal end 40 of the coil 38 can be attached to the second segment 16, 116 in some embodiments of the disclosure. At least a portion of the distal end 42 of the coil 38 can be attached to the second segment 16, 116 in some embodiments of the disclosure. The proximal and distal ends 40, 42 of the coil 38 can be attached to the second segment 16, 116 using any suitable attachment mechanism, for example, a solder joint, adhesive, thermal bonding, mechanical bonding, welding, and the like. For example and without limitation, approximately two to three turns of the coil 38 at both the proximal end 40 and at the distal end 42 can be attached to the second segment 16, 116. In accordance with an embodiment of the disclosure, two of electrodes 32, 34, 36 can be swaged upon each portion of the coil 38 that is attached to the second segment 16, 116 at proximal and distal ends 40, 42 of the coil 38 in order to help maintain the position of coil 38. Although the coil 38 is described as being attached to the second segment 16, 116 in accordance with some embodiments of the disclosure, in other embodiments of the disclosure, the coil 38 can be allowed to float more freely, lacking one or more fixed attachment points to the second segment 16, 116. The use of a relatively free floating coil 38 in accordance with some embodiments of the disclosure can be configured to allow the faces of the ends of the coil 38 to not necessarily remain perpendicular to the longitudinal axis A of the medical device 10, which can potentially alleviate "bunching" of the coil 38 where the turns overlap each other during flexing of the coil 38.

The coil 38 is further configured to maintain the hoop strength of the medical device 10, 100. Hoop strength refers to the ability of a tubular component to maintain its circumferential structural integrity. In various embodiments and still referring to FIGS. 2-4, the medical device 10, 100 may further comprise a fluid lumen 44. The fluid lumen 44 may be configured for use with fluid (e.g., saline) irrigation to cool the electrode 30 and target tissue interface during radiofrequency (RF) ablation. Irrigation fluid can be pumped through the second segment 16, 116 of the medical device 10, 110 via the fluid lumen 44. The fluid lumen 44 is disposed radially inwardly of the coil 38 in the second segment 16, 116. However, the fluid lumen 44 generally extends along the length of both the first segment 14 and the second segment 16 in accordance with an embodiment of the disclosure. The fluid lumen 44 can be located in the approximate center of the shaft 12. For example, the fluid lumen 44 can be defined by polyimide tubing in accordance with an embodiment of the disclosure. For example and without limitation, the polyimide tubing may comprise braided polyimide tubing. Polyimide tubing has a very high strength, but can easily kink and/or deform if it is bent beyond a critical angle or radius. The coil 38 is configured to avoid kinking or other deformation of the fluid lumen 44 that could otherwise cut off the flow of fluid through the fluid lumen 44 during use of the medical device 10, 100, including during buckling of the second segment 16. The coil 38 is configured to support the hoop strength of the fluid lumen 38 during buckling, which allows for an open pathway in which the fluid lumen 44 resides.

Figure 5:
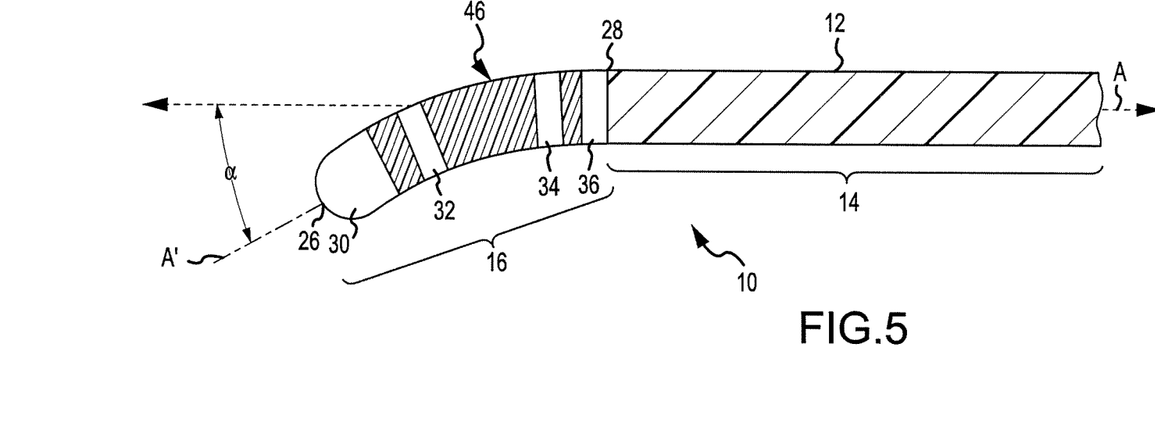
FIG. 5 is a schematic view of a medical device in accordance with a third embodiment of the disclosure.

Referring now to FIG. 5, the medical device 10, 100 can further include a deflection preference element 46 configured to preferentially buckle the second segment 16, 116 in a select manner during application of a critical force thereto in accordance with an embodiment of the disclosure. In other words, the deflection preference element 46 can comprise means for allowing the second segment 16, 116 to preferentially buckle in a select manner. For example and without limitation, the deflection preference element 46 can comprise a curve at a select location along the length of the medical device 10, 100. The curve can be relatively shallow in accordance with an embodiment of the disclosure. For example and without limitation, the curve can be in the range of up to about 15 degrees. For another example and without limitation, the curve can be in the range of about 5 degrees to about 25 degrees. Again, even though those specific exemplary curves are mentioned in detail, the range of degrees for the curve can be greater or smaller in accordance with various embodiments of the disclosure. For example and without limitation, the curve can be defined by the angle $\alpha$ between the longitudinal axis A of the first segment 14 and a longitudinal axis A' of the distal-most portion of the second segment 16, 116 as generally illustrated in FIG. 5. The deflection preference element 46 can be configured to pre-instruct the second segment 16, 116 of the medical device 10, 100 the direction and/or orientation of buckling. It may be preferable in accordance with an embodiment of the disclosure to include a deflection preference element 46 in order to control the location and direction or orientation of the buckling of the second segment 16, 116 along the length of the medical device 10, 100. For example and without limitation, it may be preferable for the buckling to occur away from the proximal end 28, 128 of the second segment 16, 116 and/or it may be preferable for the buckling to occur in a particular direction away from the longitudinal axis A of the medical device 10, 100. Although these buckling configurations are mentioned in detail, the medical device 10, 100 is configured to buckle in any location along the length of the medical device 10, 100 and/or in any direction and can accommodate on-axis forces.

Figure 6:
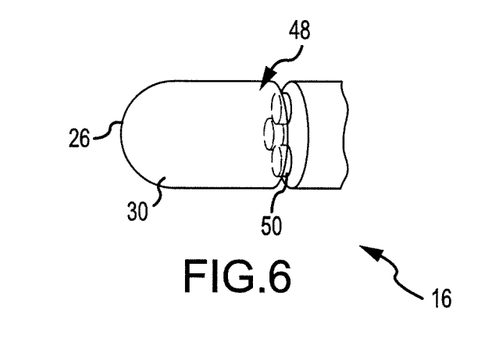
FIG. 6 is an isometric diagrammatic view of an electrode of the medical device of FIG. 1 illustrating an exemplary force/contact sensor assembly in accordance with a fourth embodiment of the disclosure.

The medical device 10, 100 can further comprise a force/contact sensor assembly 48 configured to detect an amount of force provided by the medical device 10, 100. Referring now to FIG. 6, for example and without limitation, the force/contact sensor assembly 48 can include one or more sensors 50 disposed generally adjacent a base portion of the electrode 30. The sensors 50 can be configured to measure pressure applied to the tip of the electrode 30 and provide a pressure signal indicative of the measured pressure, with the sensors 50 including a predetermined sensitivity. The electrode 30 and the remainder of medical device 10, 100 can include a predetermined flexibility so that force applied to the electrode 30 can be determinable as a function of the predetermined sensitivity and the pressure signal. For example and without limitation, the force/contact sensor assembly 48 can be substantially similar to the sensor assembly described in U.S. Patent Application Publication No. 2010/0168620 entitled "System And Method For Measuring Force And Torque Applied To A Catheter Electrode Tip," which is hereby incorporated by reference in its entirety as though fully set forth herein. The force/contact sensor assembly 48 can also be substantially similar to and/or incorporate features of the sensors described in U.S. Patent Application Publication No. 2008/0249522 entitled "Irrigated Catheter With Improved Fluid Flow," U.S. Patent Application Publication No. 2008/0275428 entitled "Optic-Based Contact Sensing Assembly and System," and/or International (PCT) Published Patent Application No. WO 2010/078453 entitled "Optic-Based Contact Sensing Assembly and System," the entire disclosures of which are incorporated herein by reference. The force/contact sensor assembly 48 can also be substantially similar to and/or incorporate features of the sensors described in U.S. Patent Application Publication No. 2011/0022045 entitled "Ablation Electrodes With Capacitive Sensors for Resolving Magnitude and Direction of Forces Imparted to a Distal Portion of a Cardiac Catheter," U.S. Patent Application Publication No. 2008/0161796 entitled "Design of Ablation Electrode With Tactile Sensor," U.S. Patent Application Publication No. 2008/0015568 entitled "Dynamic Contact Assessment for Electrode Catheters," U.S. Patent Application Publication No. 2007/0123764 entitled "Systems and Methods for Assessing Tissue Contact," and U.S. Patent Application Publication No. 2007/0100332 entitled "Systems and Methods for Electrode Contact Assessment," the entire disclosures of which are incorporated herein by reference.

In accordance with some embodiments of the disclosure, the sensor assembly 48 can be operatively connected to a signal converter (not shown) and/or an operator interface (not shown), which can further include a computer and a display, for processing the pressure signals received in connection with positioning and contacting targeted tissue. This information can be processed to determine the contact force exerted on the electrode 30. A calibration system (not shown) can be further provided to readily correlate the pressure measurements to the external force or torque on the electrode 30. A navigation, visualization, and/or mapping system, such as the ENSITE NAVX™ system mentioned above and generally available from St. Jude Medical, Inc., can be integrated and/or used with the sensor assembly 48.

Although one exemplary force/contact sensor assembly 48 is described in detail, other force/contact sensor assemblies can be used in accordance with other embodiments of the disclosure. For example and without limitation, another approach for sensing contact is to assess the degree of electrical coupling, for example, in an electrical coupling index (ECI) between a sensing element and the surface, as seen by reference to, for example, U.S. patent application Ser. No. 12/253,637, now U.S. Patent Application Publication No. 2009/0163904 entitled "System and Method for Assessing Coupling Between an Electrode and Tissue," which is incorporated herein by reference in its entirety as though fully set forth herein. The ENSITE NAVX™ system mentioned above and generally available from St. Jude Medical, Inc. can estimate contact between an ablation electrode and the targeted tissue based on local impedance measurements, and this calculation is termed the ECI. In other words, the ECI can be derived from the complex impedance measurement. Research has shown that there can be a correlation between the ECI and force contact, and a computer can be used to process the ECI information to determine the contact force exerted on the electrode 30 in some embodiments of the disclosure. The ECI can be subject to variability based on changes to properties associated with patient bodies (e.g., differences in body temperature among patients) and components of the system (e.g., differences resulting from the use of different ablation catheters).

In some embodiments of the disclosure, the medical device 10, 100 can be configured into an implicit contact force sensor. Under this approach, monitoring a bend angle between critical sections of the segments 14, 16, 116 of the medical device 10, 100 can be used for sensing force and/or contact. For example, in those embodiments of the disclosure having about four electrodes as generally illustrated in FIG. 4, the proximal two electrodes 34, 36 can be disposed on a first critical section 37, and the distal two electrodes 30, 32 can be disposed on a second critical section 39. A bend angle $\beta$ between the axial line $L_1$ defined by electrodes 34, 36 and the axial line $L_2$ defined by electrodes 30, 32 may be proportional to contact force. The bend angle $\beta$ can be continuously monitored using a visualization, navigation, and/or mapping system such as those systems available under the name ENSITE NAVX™ (aka ENSITE™ 'Classic' as well as newer versions of the ENSITE™ system, denoted as ENSITE VELOCITY™) and available from St. Jude Medical, Inc. In other words, the electrode pairs 30, 32, and 34, 36 may serve as position and/or orientation sensors configured to generate a signal indicative of the bend angle $\beta$. Alternatively, if magnetic field sensors (e.g., coils) are disposed in the medical device 10, 100 for use with a magnetic tracking system such as the system available under the name MEDIGUIDE™ and available from St. Jude Medical, Inc., the bend angle $\beta$ between the lines $L_1$, $L_2$ defined by electrodes 30, 32, 34, 36 can be continuously monitored using the magnetic tracking system. A calibration system (not shown) can be provided to readily correlate the measurements for the bend angle $\beta$ to the external force or torque on the medical device 10, 100, and/or a computer can be used to process the bend angle $\beta$ to determine the contact force exerted on the medical device 10, 100 in some embodiments of the disclosure.

In accordance with an embodiment of the disclosure, the pressure measurements and/or force measurements can be used to modify and/or control the advancement of the medical device 10, 100 to achieve a desired amount of contact/force between the medical device 10, 100 and targeted tissue. Movements of the chest and heart, due to respiratory and pumping function, can cause problems in ensuring optimal contact between the medical device 10, 100 and the targeted tissue. For example and without limitation, the targeted tissue may be moving as with, for example, the beating of the heart. The use of the pressure measurements and/or force measurements can help ensure constant contact and/or desired amount of force between the medical device 10, 100 and targeted tissue by advancing and/or retracting the medical device 10, 100 a select distance as needed to ensure contact and/or desired force with the moving body structure. Such an embodiment of the disclosure may be especially useful in connection with robotically controlled medical devices. In accordance with such an embodiment, an electronic control unit (ECU) (not shown) can be used in connection with the sensor assembly 48 and the medical device 10, 100. A display device (not shown) can also be used in connection with the sensor assembly 48 and the medical device 10, 100 and the ECU.

The ECU comprises a programmable microprocessor or microcontroller, but can alternatively comprise an application specific integrated circuit (ASIC). The ECU can include a central processing unit (CPU) and an input/output (110) interface through which the ECU can receive input data (e.g., pressure measurements from sensor assembly 48) and can generate output data (e.g., force measurements and/or select distances for advancement and/or retraction of medical device 10, 100). The ECU can also have a memory. The input data and output data acquired and generated by the ECU can be stored in the memory of the ECU. As described above, the input data can include the pressure measurements obtained by the sensor assembly 48. The input data can further include information regarding the sensitivity of the sensor assembly 48 and/or the flexibility of the medical device 10, 100 or portions thereof. As described above, the output data can include select distances for advancement and/or retraction of medical device 10, 100. The ECU and display device can also be connected to a control system (not shown). The control system can be configured to adjust the advancement/retraction of the medical device 10, 100 based at least in part on the force/contact sensing in accordance with an embodiment of the disclosure. For example, if the sensor assembly 48 (or other system described herein) senses a decrease in contact/force, then the control system may be configured to advance the medical device 10, 100 toward the targeted tissue. However, if the sensor assembly 48 senses an increase in contact/force, then the control system may be configured to retract the medical device 10, 100 away from the targeted tissue. The sensor assembly 48 can thus provide feedback which can be implemented in a control algorithm executed by the ECU and/or control system to automatically control the movement (e.g., advancement/retraction) of the medical device 10, 100. As a safety measure, when the pressure readings from the sensor assembly 48 exceed a predetermined or select threshold value, the control system can be configured to prevent further actuation and/or advancement of the medical device 10, 100. Alternatively or additionally, the sensed pressure and/or force can be displayed to the user with or without a warning (e.g., visual or audible). In some embodiments, a robotic or remote catheter guidance system, such as that described in one or more of the following, may be employed to perform some, or all, of the above stated functions: U.S. Patent Application Publication No. 2009/0247942, published Oct. 1, 2009 and entitled "Robotic Catheter Manipulator Assembly"; U.S. Patent Application Publication No. 2009/0247944, published Oct. 1, 2009 and entitled "Robotic Catheter Rotatable Device Cartridge"; U.S. Patent Application Publication No. 2009/0247993, published Oct. 1, 2009 and entitled "Robotic Catheter System"; U.S. Patent Application Publication No. 2009/0248042, published Oct. 1, 2009 and entitled "Model Catheter Input Device"; International Published Patent Application No. WO 2009/120982, published Oct. 1, 2009 and entitled "Robotic Catheter System With Dynamic Response"; U.S. Patent Application Publication No. 2010/0256558, published Oct. 7, 2011 and entitled "Robotic Catheter System"; and U.S. patent application Ser. No. 12/933,063 filed Sep. 16, 2010 and entitled "Robotic Catheter System Input Device", the entire disclosures of which are incorporated herein by reference.

Although at least five embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device comprising:
    a shaft comprising an axis and comprising a first, proximal segment and a second, distal segment, and wherein said second, distal segment includes a proximal end and a distal end,
        wherein the first, proximal segment is configured to buckle upon application of a first critical force thereto, wherein the first critical force is between about 200 grams-force and about 660 grams-force;
        wherein the second, distal segment includes an outer surface and an inner surface and is configured to buckle upon application of a second critical force thereto that is lower than the first critical force; and
    a coil disposed radially inwardly of the inner surface of the second, distal segment, said coil being disposed within said second, distal segment, said coil being separate from said first, proximal segment, said second, distal segment being further configured to limit the amount of force transmitted by the second, distal segment to tissue in a body of a patient contacting the second, distal segment after an application of the second critical force to the second, distal segment as the device is advanced over a distance toward the tissue;
    a field sensor located on or within the shaft responsive to a magnetic field generated by a medical positioning system wherein the field sensor is configured to output to an external computer or processor an electrical field sensor signal indicative of at least one of a position and an orientation of the field sensor within the body; and
    electric conductors, wherein said electric conductors are electrically coupled to said field sensor and are also configured to be electrically coupled to the external computer or processor.

2. The medical device of claim 1 wherein the field sensor comprises a conductive coil.

3. The medical device of claim 2 wherein the field sensor comprises a magnetic field detection coil, the medical positioning system (MPS) being configured to generate the magnetic field as a changing magnetic field, and wherein a voltage corresponding to the field sensor signal is induced in the magnetic field detection coil when residing in the changing magnetic field.

4. The medical device of claim 3 wherein the field sensor comprises a plurality of magnetic field detection coils.

5. The medical device of claim 3 wherein the changing magnetic field comprises an alternating current (AC) magnetic field.

6. The medical device of claim 1 further comprising an electrode disposed on the distal end of the second, distal segment, the electrode comprising a positioning electrode configured to produce a representative signal indicative of at least one of a position and orientation thereof.

7. The medical device of claim 6 wherein the positioning electrode is further configured to sense an impedance.

8. The medical device of claim 6 wherein the electrode comprises a first electrode and the positioning electrode comprises a first positioning electrode, said medical device further comprising a second electrode disposed on the second, distal segment and being disposed proximally of the first electrode, and a third electrode disposed on the second, distal segment and being disposed proximally of the second electrode, wherein the first, second, and third electrodes comprise electrically conductive material, the second and third electrodes comprising second and third positioning electrodes.

9. The medical device of claim 8 wherein the coil is positioned between the second and third electrodes.

10. The medical device of claim 1 wherein the second critical force is between an amount of force required to create a transmural lesion and that capable of causing a perforation of the tissue.

11. The medical device of claim 10 wherein the amount of force required to create the transmural lesion is within a range between 20 to 50 grams-force and that capable of causing the perforation of the tissue is within a range between 50 to 100 grams-force.

12. The medical device of claim 1 wherein the second critical force is in the range of about 40 grams-force to about 100 grams-force.

13. The medical device of claim 1 wherein the second, distal segment has a hardness between about 25 and about 35 on a Shore D scale.

14. The medical device of claim 1 further comprising a fluid lumen disposed radially inwardly of the coil.

15. The medical device of claim 1 further comprising a force/contact sensor configured to detect an amount of force provided by the medical device.

16. The medical device of claim 1 wherein the coil is free and unattached relative to the second, distal segment.

* * * * *